United States Patent [19]

Grafelmann

[11] Patent Number: 4,863,383
[45] Date of Patent: Sep. 5, 1989

[54] SELF-TAPING SCREW-IN BONE IMPLANT FOR DENTAL PURPOSES

[76] Inventor: Hans L. Grafelmann, Parkstrasse 105 D-2800, Bremen 1, Fed. Rep. of Germany

[21] Appl. No.: 169,469

[22] Filed: Mar. 17, 1988

[30] Foreign Application Priority Data

Mar. 17, 1987 [DE] Fed. Rep. of Germany ....... 3708638

[51] Int. Cl.⁴ ............................................. A61C 13/00
[52] U.S. Cl. .................................................. 433/174
[58] Field of Search ............................... 433/173, 174

[56] References Cited

U.S. PATENT DOCUMENTS

| | | | |
|---|---|---|---|
| 2,472,103 | 6/1949 | Giesen | 433/174 |
| 4,406,623 | 9/1983 | Grafelmann et al. | 433/174 |
| 4,486,178 | 12/1984 | Schulte et al. | 433/174 |
| 4,713,004 | 12/1987 | Linkow et al. | 433/174 |

*Primary Examiner*—Robert Peshock
*Attorney, Agent, or Firm*—Balough, Osann, Kramer, Dvorak, Genova & Traub

[57] ABSTRACT

The implant for dental purposes comprises a socket (4) and is provided with self-tapping screw threads, which are screwed into a pilot bore formed in the jaw bone. The socket receives a post (10), which has a stem (13) and is adapted to carry dental suprastructures. The stem (13) of the post is provided at its inner end with male screw threads (16), which have been screwed into female screw threads formed in the socket. In accordance with the invention the crest diameter of the self-tapping screw threads is equal throughout the axial length of said screw threads to the diameter of the socket (4) at its outer end. The self-tapping screw threads are formed on an axially inwardly tapering shank and continuously decrease in depth to zero from the inner end of said self-tapping screw threads to the outer end of the socket (4) or to a point which is spaced 2 to 3 mm from the outer end of said socket.

5 Claims, 2 Drawing Sheets

SELF-TAPING SCREW-IN BONE IMPLANT FOR DENTAL PURPOSES

BACKGROUND OF THE INVENTION

1. Field of the Invention

This invention relates to a self-tapping screw-in bone implant for dental purposes.

When posts are to be anchored for a fixation of dental suprastructures, such as bridges or weblike stiffeners, implants are inserted or screwed into a pilot bore, which has been drilled into the jaw bone. A screw-in bone implant comprises a post-receiving socket and a tapering shank which is integral with said socket and said implant is formed on its outside peripheral surface with self-tapping sharp-edged screw threads having a large lead. The socket has a socket opening formed with female screw threads for threaded engagement with a post.

2. Description of the Prior Art

Implants of that kind are known from Published German Application No. 3,136,602 and have self-tapping screw threads on a tapered shank. The screw threads have also a taper, which differs from that of the shank. The shank of that known implant is small in diameter (about 2 mm) and its screw threads have a large depth and a radius which increases progressively from the tip. The bone portions which are displaced by the screw threads during the tapping operation are received by the trabecular framework of the laterally adjacent bone portions. That implant is intended to be axially supported in the jaw by compact bone portions at the tip of the shank. They are more suitable for spongious or cancellous bone.

SUMMARY OF THE INVENTION

It is an object of the invention to provide an implant which is of the kind described first hereinbefore and which will contact the bone around the bore on a larger surface area and reliably to close the free annular space between the bore-defining bone surface and the implant from the beginning of the screwing operation and to preclude a permanent compression of the bone by the screw threads.

It is a specific object of the invention to provide such an implant which will establish a uniform contact between the bone and the bone implant in a wide area from the very beginning of the insertion of the implant and particularly in the region in which the implant emerges from the bone and contacts the gingiva, i.e., in the upper portion of the bore which receives the implant. In that region the bone may also be contacted by a threadless polished annular surface of the implant in an axial length of 2 to 3 mm; that annular surface has the same diameter as the surrounding portion of the receiving bore. The threads may also extend over the complete implant or up to the region in which the implant emerges from the bone, i.e., up to the socket entrance.

It is a further object of the invention to provide an implant of the kind described which can be used in jaw regions in which an axial support of the bone by compact bone portions at the tip of the shank cannot be relied upon because the implant can be supported by its screw threads in the laterally adjacent bone portions, particularly near the tip, even if they are spongy. The immediate stabilization effect in compact bone substance is easier to obtain due to the deeper threads in the opex region.

The objects stated above are accomplished in the implant in accordance with the invention in that the crest diameter of the self-tapping screw threads of the implant is not in excess of the diameter of the socket throughout the axial length of said screw threads. The entire implant is like a geometric cylinder including the threads outside diameter.

The entire implant preferably has a constant diameter throughout its length. That shape is preferably achieved in that the depth of the screw threads continuously decreases to zero in the direction from the tip of the shank to the outer end of the socket.

Alternatively, the implant may have a slight taper toward the tip of the shank.

The same object may be accomplished in a manner which is known from published German Application No. 31 36 602 in that the self-tapping screw threads are formed with indentations, which are angularly spaced less than 360° in such a manner that the average number of recesses per 360° is two. In that case the self-tapping screw threads do not have in axial section the configuration of an isosceles triangle but that side face of the screw threads which faces the tip of the shank includes with the axis of the shank an angle not in excess of 90° and the other side face includes with the axis of the shank an obtuse angle of about 120°.

The same object can be accomplished in that the core is formed with one or more indentations, which extend into the apical-bicortical supporting tip of the implant. The sharp shorter outer edge of said indentation or each of said indentations defines a surface which faces in the sense in which the implant is rotated as it is screwed into the bore.

The socket is formed with a hexagonal recess for engagement by a wrench used to rotate the implant into the bore in the bone and at the bottom of said recess is formed with a blind bore, which has female screw threads so that a temporarily used post for promoting the healing or a cover screw or at a later time, a permanent post, can be screwed into the socket. Said posts are provided with male screw threads on a stem which extends through the hexagonal socket opening.

The implant is screwed into the bore formed in the bone until the outer end of the socket is flush with the outside surface of the surrounding bone or protrudes 1 to 2 mm from said outside surface and the tip of the implant contacts and may be axially supported by the adjacent surface of compact bone, although such support at the tip is not essentially required. If a temporary post is to be inserted, its length will be so selected that its top surface is flush with the top surface of the adjacent gingiva.

Instead of a temporary post which protrudes from the socket of the implant to the extent of the thickness of the gingiva, a more shallow cover screw may selectively be used in known manner. That cover screw is formed at its top with a slot, which is engageable by a screwdriver for screwing such cover screw into and out of the socket. In that case the gingiva will grow to completely cover the implant.

When screw-threaded implant posts which have been screwed in are finished with burs which rotate in a clockwise sense, the engagement of the screw threads may be loosened as a result of the vibration and under the action of the finishing bur driven, e.g., by a right-turning air turbine, the post will be unscrewed in a counterclockwise sense. In accordance with the invention this can be prevented in that the female and male screw-threads are left-handed.

DETAILED DESCRIPTION OF THE PREFERRED EMBODIMENT

Figure 1:
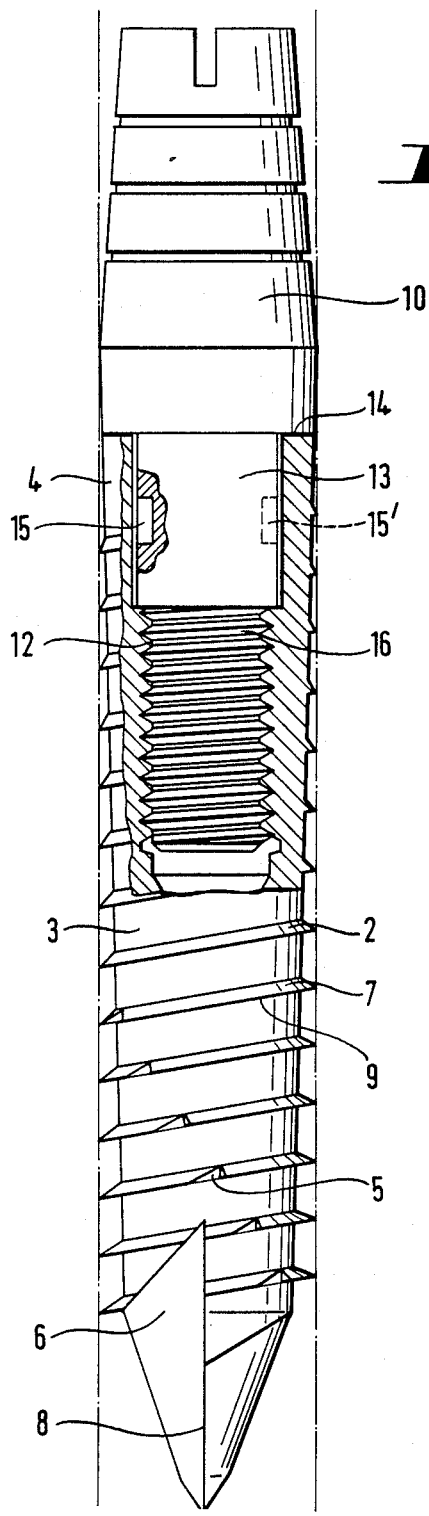
FIG. 1 is an elevation showing an implant assembly embodying the invention with a broken away socket and a screwed-in permanent post, which has retaining grooves and a screwdriver slot. The cylindrical outside peripheral surfaces at the butt joint between the post and the implant are flush.
Figure 2:
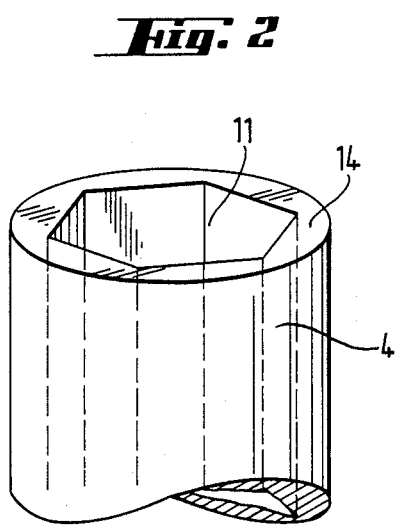
FIG. 2 is a perspective view showing the top end portion of the implant with the hexagonal portion of the socket opening.

A preferred embodiment of an implant in accordance with the invention is shown diagrammatically and partly in section on the drawing.

The implant shown in the drawing comprises a screw 1, which is formed with sharp-edged screw threads 2 on a tapered shank 3. The shank 3 is integral with a socket 4, on which the self-tapping screw threads 2 are continued. In accordance with the invention the depth of the screw threads 2 continuously decrease to zero in the direction from the tip of the shank 3 to the outer end of the socket 4 so that the outside diameter of the rod-shaped implant remains constant from its top to the inner end of the screw threads 2.

A zero depth of the screw threads is reached 2 to 3 mm below the butt joint 14.

Figure 3:
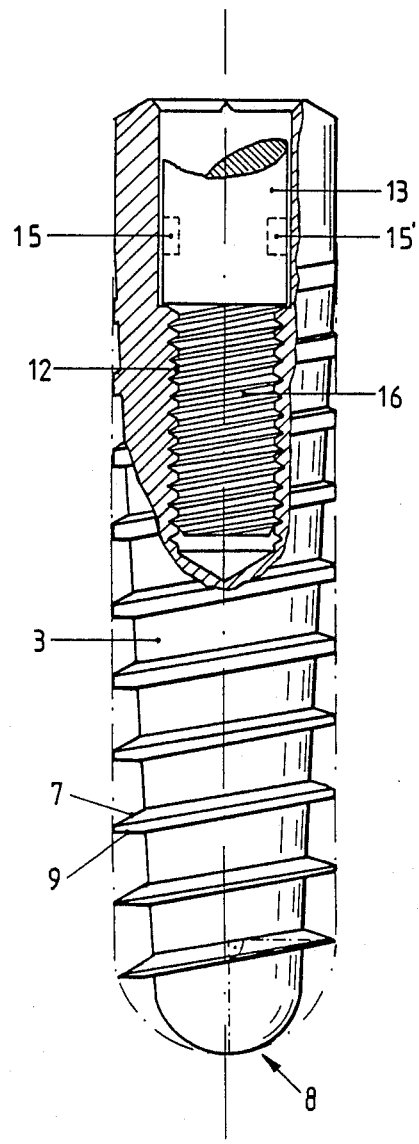
FIG. 3 is an elevation showing the partly cut screw threads on the shank.
Figure 4:
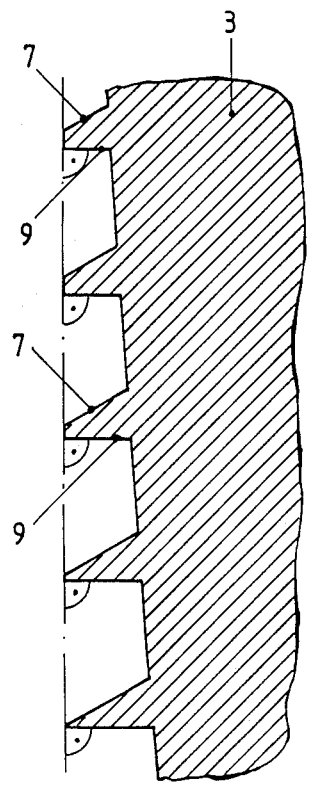
FIG. 4 is a longitudinal sectional view showing the screw threads on the shank on a larger scale than in FIG. 3.

To facilitate the self-tapping operation, one or more indentations 5 are formed in each convolution of the screw threads 2. For the same purpose the shank 3 if formed in its tip portion with notches 6, each of which has a sharp edge which extends generally in the longitudinal direction of the shank and defines a surface that faces in the sense in which the implant is rotated as it is screwed into the bore. The profile of the screw threads 2 is shown in FIGS. 3 and 4. Those side faces 9 of the screw threads which face the tip of the shank 3 are at right angles to the axis of the shank and those side faces 7 which face the socket 4 include an obtuse angle with said axis.

The post 10 comprises a stem 13, which at its inner end carries male screw threads 16. The socket 4 has a socket opening 11, which has a non-circular outer portion, which may be hexagonal as shown in the illustrated embodiment, and which is engageable by a mating socket key. The socket opening 11 comprises at its inner end a blind circular bore, which is formed with female screw threads 12. The male screw threads 16 of the stem 13 of the post 10 are screwed into the female screw threads 12. Those portions of the socket 4 and of the post 10 which abut at the joint 14 have cylindrical outside peripheral surfaces which are equal in diameter and flush with each other.

To permit the post 10 to be secured in the socket 4, the stem 13 of the post 10 is formed with recesses 15, 15' for receiving adhesive paste or cement of the like, which will prevent a rotation of the post. For the reasons stated hereinbefore the female screw threads 12 and the male screw threads 16 of the stem 13 may be left-handed.

The socket 4 has at its outer end a circular outside rim, which is adjoined by a threadless cylindrical outside peripheral surface having an axial width of 2 to 3 mm. The socket 4 tapers from said cylindrical outside surface to the shank 3. The self-tapping screw threads 2 terminate at said cylindrical outside surface.

The novel screw implant disclosed hereinbefore affords the following advantages:

It is not necessary to insert the implant in the manner which is usual with the conventional implants, i.e., to drill such a bore into the bone so that only the crests of the screw threads will contact the bone surfaces defining the bore, or to initially drill a narrow pilot bore, which is then enlarged to a diameter which will permit the larger screw threads to cut into the bone, or to use a thread cutter instrument to pre-cut the threads in the bone.

The implant will easily be self-tapping even in a high-crest bone, in which an inherently fixed center line is required.

Because the post consists of a separate part, it is possible to fix the post to the implant after the bone has healed around the implant. The post which is subsequently attached can be selected from a large assortment.

Alternatively, a healing post can temporarily be attached to ensure that the gingiva will be kept open during the healing time.

Because a post which is equal in diameter to the socket can be used with the novel implant, it is possible to use only one caliber shaft drill that relates to the outer implant diameter and the conical inside shank, which results in an immediate and tight bore contact.

The special design of the screw threads ensures that the inserted implant will gently compress and will adhere to the bone from the entrance of the bore over a predetermined length, from the very first movement.

The special design of the screw threads will also result in a self-tapping action at the beginning of the insertion and in an adhesion when the implant has been fully inserted.

I claim:

1. In a self-tapping screw implant for fixing a post for anchoring a dental suprastructure, comprising
    a socket, which has at its outer end a circular outside rim and is formed with an axially extending socket opening, which is open at said outer end, and
    a shank, which is integral with said socket and has a tip which is opposite to said socket, wherein said shank tapers in the direction from said socket to said tip and is formed with self-tapping screw threads having a sharp-edged crest,
    the improvement residing in that the diameter of said crest is not in excess of the diameter of said outside rim at any point of the axial length of said screw threads, wherein
    the diameter of said crest is equal to the diameter of said outside rim throughout the axial length of said screw threads.

2. The improvement set forth in claim 1, wherein the diameter of said crest is constant throughout the axial length of said screw threads.

3. The improvement set forth in claim 1, wherein said screw threads have a depth which continuously decreases to zero in the direction from said tip to said outer end of said socket.

4. The improvement set forth in claim 3, wherein the depth of said screw threads continuously decreases to zero from said tip as far as to said socket.

5. The improvement set forth in claim 3, wherein the depth of said screw threads continuously decreases to zero from said tip to a point which is spaced about 3 mm from said socket.

* * * * *